United States Patent
Haddadin

(10) Patent No.: US 10,952,876 B2
(45) Date of Patent: Mar. 23, 2021

(54) PROSTHESIS

(71) Applicant: Cavos Bagatelle Verwaltungs GmbH & Co. KG, München (DE)

(72) Inventor: Sami Haddadin, Hannover (DE)

(73) Assignee: Cavos Bagatelle Verwaltungs GmbH & Co. KG, Munich (DE)

(*) Notice: Subject to any disclaimer, the term of this patent is extended or adjusted under 35 U.S.C. 154(b) by 64 days.

(21) Appl. No.: 16/095,115

(22) PCT Filed: Apr. 25, 2017

(86) PCT No.: PCT/EP2017/059699
§ 371 (c)(1),
(2) Date: Oct. 19, 2018

(87) PCT Pub. No.: WO2017/186659
PCT Pub. Date: Nov. 2, 2017

(65) Prior Publication Data
US 2019/0117416 A1 Apr. 25, 2019

(30) Foreign Application Priority Data
Apr. 25, 2016 (DE) .................... 10 2016 107 615.5

(51) Int. Cl.
*A61F 2/72* (2006.01)
*A61F 2/54* (2006.01)
(Continued)

(52) U.S. Cl.
CPC ............. *A61F 2/72* (2013.01); *A61F 2/54* (2013.01); *A61F 2/60* (2013.01);
(Continued)

(58) Field of Classification Search
CPC ............. A61F 2/72; A61F 2/54–646; A61F 2002/5006; A61F 2002/5036;
(Continued)

(56) References Cited

U.S. PATENT DOCUMENTS 8,828,093 B1 9/2014 Kuiken et al.
2004/0049290 A1 3/2004 Bedard
(Continued)

FOREIGN PATENT DOCUMENTS

DE 102009056466 A1 6/2011
JP 2008-212652 A 9/2008
(Continued)

OTHER PUBLICATIONS

English translation of the International Preliminary Report on Patentability dated Nov. 8, 2018 for International Application No. PCT/EP2017/059699.

*Primary Examiner* — Suba Ganesan
*Assistant Examiner* — Aren Patel
(74) *Attorney, Agent, or Firm* — Hoffmann & Baron, LLP

(57) ABSTRACT

Prosthesis including prosthetic links driven by actuators, first sensors that sense current state ZUS(t); second sensors that sense biosignals $SIG_{BIO}(t)$; third sensors that sense data $D_{UMG}(t)$; processing device; and memory storing instructions that, when executed by the processing device, perform operations including: determining based on $SIG_{BIO}(t)$, ZUS(t), and $D_{UMG}(t)$, model $M_A(t)$ of an action A, and predicting motions $B_{eweg}(M_A(t))$, dependent on $M_A(t)$ for a time period; determining a decision E to replace A with an action A'(E) based on $SIG_{BIO}(t)$, ZUS(t), $D_{UMG}(t)$, and $B_{eweg}(M_A(t))$ according to an evaluation scheme, wherein A'(E) can define a reflexive and/or protective motion, and if A'(E) does not define the reflexive and/or protective motion, then determining model $M_{A'}(t)$ of A'(E) and predicting motions $B_{eweg}(M_{A'}(t))$, dependent on $M_{A'}(t)$, for the time period; deriving control signals Sig(t) based on $B_{eweg}(M_A(t))$ or $B_{eweg}(M_{A'}(t))$, or based on the reflexive and/or protective motion, and controlling/regulating the actuators based on Sig(t).

14 Claims, 1 Drawing Sheet

(51) Int. Cl.
*A61F 2/60* (2006.01)
*A61F 2/50* (2006.01)
*A61F 2/70* (2006.01)
*A61F 2/76* (2006.01)
*A61F 2/68* (2006.01)

(52) U.S. Cl.
CPC ............... *A61F 2002/5006* (2013.01); *A61F 2002/5036* (2013.01); *A61F 2002/689* (2013.01); *A61F 2002/6809* (2013.01); *A61F 2002/701* (2013.01); *A61F 2002/704* (2013.01); *A61F 2002/762* (2013.01); *A61F 2002/764* (2013.01); *A61F 2002/766* (2013.01); *A61F 2002/7615* (2013.01); *A61F 2002/7625* (2013.01); *A61F 2002/7635* (2013.01); *A61F 2002/7645* (2013.01); *A61F 2002/7665* (2013.01)

(58) Field of Classification Search
CPC ........ A61F 2002/6809; A61F 2002/689; A61F 2002/701; A61F 2002/704; A61F 2002/7615; A61F 2002/762; A61F 2002/7625; A61F 2002/7635; A61F 2002/764; A61F 2002/7645; A61F 2002/766; A61F 2002/7665
USPC .......................................................... 623/25
See application file for complete search history.

(56) References Cited

U.S. PATENT DOCUMENTS

| | | |
|---|---|---|
| 2008/0211302 A1 | 9/2008 | Hirota et al. |
| 2010/0324699 A1* | 12/2010 | Herr .................... A61F 2/66 623/27 |
| 2012/0004736 A1 | 1/2012 | Goldfarb et al. |
| 2012/0221119 A1 | 8/2012 | Goldfarb et al. |
| 2014/0031952 A1* | 1/2014 | Harshbarger .......... A61F 2/54 623/25 |
| 2014/0058528 A1* | 2/2014 | Contreras-Vidal .......... A61B 5/0496 623/25 |
| 2014/0081421 A1* | 3/2014 | Herr .................... A61H 3/00 623/25 |
| 2014/0288703 A1 | 9/2014 | Takagi |
| 2014/0336781 A1 | 11/2014 | Katyal et al. |
| 2015/0257903 A1 | 9/2015 | Perry et al. |
| 2016/0143751 A1* | 5/2016 | Chestek .................. A61F 2/72 623/25 |

FOREIGN PATENT DOCUMENTS

| | | |
|---|---|---|
| JP | 2009-112447 A | 5/2009 |
| JP | 2014-184526 A | 10/2014 |
| WO | WO 2011/066940 A1 | 6/2011 |
| WO | WO 2015/006235 A1 | 1/2015 |

* cited by examiner

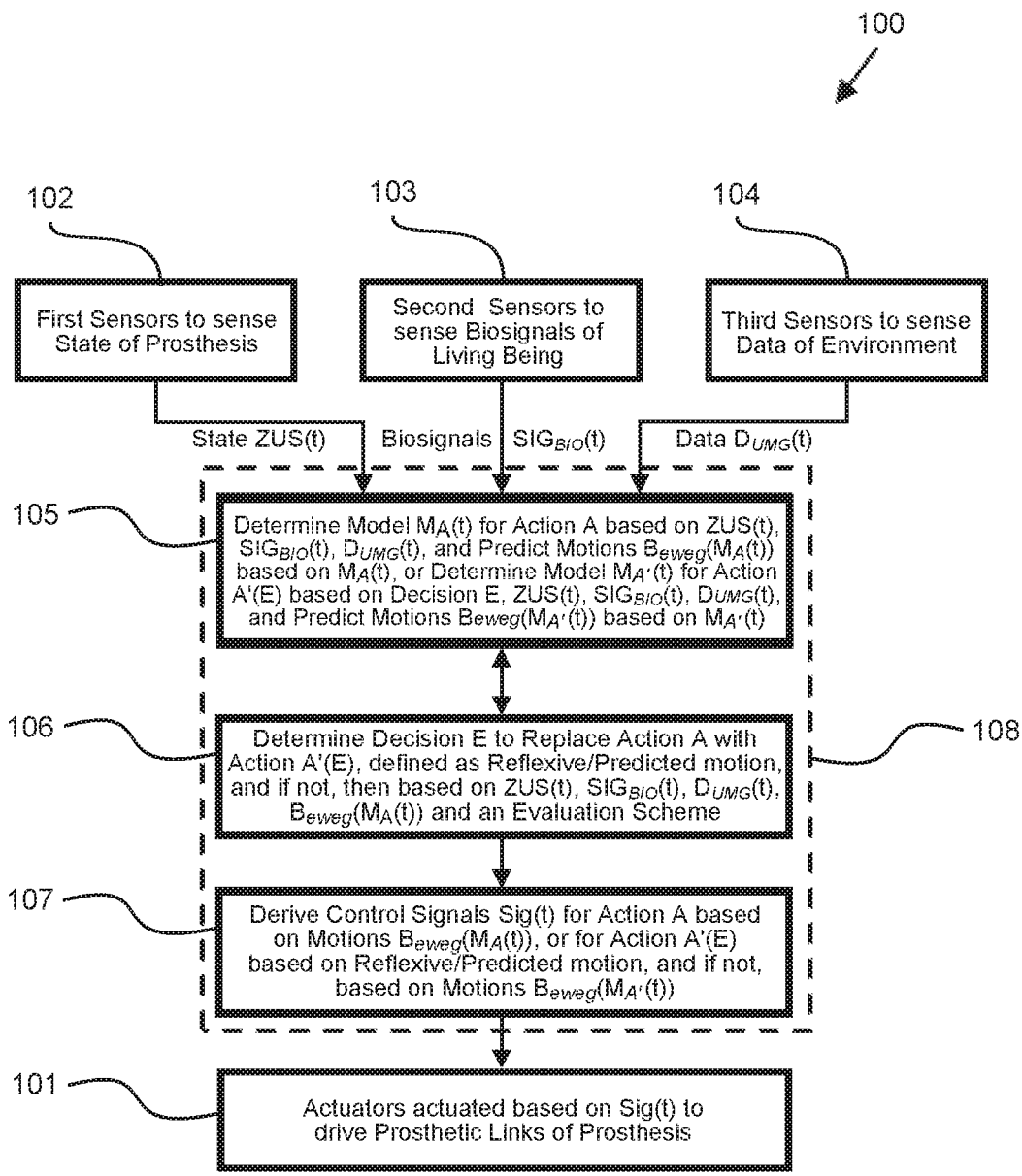

PROSTHESIS

CROSS-REFERENCE TO RELATED APPLICATIONS

This application is the U.S. National Phase of International Patent Application No. PCT/EP2017/059699, filed on 25 Apr. 2017, which claims benefit of German Patent Application No. 102016107615.5, filed on 25 Apr. 2016, the contents of which are incorporated herein by reference in their entirety.

BACKGROUND

Field

The invention relates to a prosthesis for replacing a missing extremity of a living being, particularly a human being. The prosthesis has prosthetic links driven by actuators.

Related Art

The prostheses driven by actuators available today, for example hand/arm prostheses, are associated with high procurement costs. Moreover, these prostheses are limited in their function.

SUMMARY

The object of the invention is to provide an improved prosthesis to replace a missing extremity of a living being, particularly a human being, which is economical to produce and has expanded functionality.

The invention results from the features of the main claims. Advantageous further embodiments and designs are the subject matter of the dependent claims. Further features, application options, and advantages of the invention result from the following description, and explanation, of example embodiments of the invention, which are represented in the figures.

The invention is achieved with a prosthesis for replacing a missing extremity of a living being, particularly a human being. The proposed prosthesis includes one or more prosthetic links driven by actuators, wherein the proximal prosthetic link has a mechanical interface for fixing the proximal prosthetic link to the living being.

The prosthesis further includes first sensors, which sense a current state $ZUS(t)$ of the prosthesis, particularly a state of contact between the prosthesis and the environment. Advantageously, the first sensors include one or more of the following sensors: joint sensor(s) for sensing a motor position and/or a motor speed and/or a motor acceleration, output sensor(s) for sensing an output position and/or an output speed and/or an output acceleration, acceleration sensor(s), for example for sensing an acceleration in the joints of the prosthesis or an acceleration in the prosthetic links, the acceleration due to gravity, an acceleration and motion of the mechanical interface for fixing the proximal prosthetic link, a relative acceleration and motion of the prosthesis on the residual limb, force sensor(s) for determining the forces transferred to an environment due to the individual prosthetic links and for determining forces transferred from an environment onto the individual prosthetic links, as well as for determining interaction forces between the prosthesis and the prosthesis wearer, torque sensor(s) for determining the torques transferred to an environment by the individual prosthetic links and for determining torques transferred from an environment to the individual prosthetic links, tactile sensor(s), particularly an artificial skin, for local sensing of acting forces and torques, temperature sensor(s) for sensing temperatures acting upon the prosthesis, humidity sensor(s) for sensing humidity acting upon the prosthesis. All sensors (including individual ones) may also advantageously be used to determine mechanical relations (forces, accelerations, etc.).

The prosthesis further includes second sensors, which sense biosignals $SIG_{BIO}(t)$ in the living being for controlling the missing extremity. The second sensors advantageously include one or more electromyography sensors and/or one or more electroencephalography sensors. The individual second sensors are advantageously either applied to the living being or implanted in the living being.

The prosthesis further include third sensors for sensing data $D_{UMG}(t)$, which describe a current environment of the prosthesis, particularly objects and/or other living beings located in the environment. The third sensors may include one or more of the following sensors: optical sensors, for example camera or video sensors, ultrasound sensors, laser sensors, etc.

The prosthesis further include a prediction unit, which determines a model $M_A(t)$ of an action A to be performed by the prosthesis based on the biosignals $SIG_{BIO}(t)$, the state $ZUS(t)$ of the prosthesis, and the data $D_{UMG}(t)$, and which predicts motions $B_{eweg}(M_A(t))$, dependent on the model $M_A(t)$, of the prosthetic links for a time period $[t, t+\Delta t]$. In the simplest case, the prediction takes place for a next period of time. This can be a control cycle or control cycles of the prosthesis. The prediction time period $\Delta t$ is advantageously selected in a range of from 0.3 seconds to 30 seconds. The prediction time period $\Delta t$ may advantageously vary depending on the processor load in the prediction unit. Advantageously, the prediction unit is designed and set up such that the sensing of model $M_A(t)$ and/or $M_{A'}(t)$ is implemented as a learning-capable process, which autonomously learns motions $B_{eweg}(M_A(t))/B_{eweg}(M_{A'}(t))$ of the prosthetic links based on historical data, for executing an action A/A'(E). They may also consider predicted/estimated contact and/or other multimodal information.

The prosthesis further includes an evaluating unit, which can determine the discrete decision E to replace the action A with another action A'(E) based on an evaluation of the biosignals $SIG_{BIO}(t)$, the state $ZUS(t)$, the data $D_{UMG}(t)$, and the predicted motions $B_{eweg}(M_A(t))$ in accordance with a specified evaluation scheme, wherein the action A'(E) can define a reflexive motion and/or protective motion of the prosthesis that is autonomously controlled in an open-loop/closed-loop manner, and wherein, if the action A'(E) does not define such a reflexive motion and/or protective motion of the prosthesis that is autonomously controlled in an open-loop/closed-loop manner, the prediction unit determines a model $M_{A'}(t)$ of the action A'(E) to be performed by the prosthesis and predicts motions $B_{eweg}(M_{A'}(t))$, dependent on the model $M_{A'}(t)$, of the prosthetic links for a time period $[t, t+\Delta t]$.

The evaluating unit is advantageously designed and set up such that the decision E for the action A'(E), which defines a reflexive motion and/or protective motion of the prosthesis that is autonomously controlled in an open-loop/closed-loop manner independently of the biosignals $SIG_{BIO}(t)$, is determined based on the current state $ZUS(t)$ and/or the data $D_{UMG}(t)$.

The evaluating unit is advantageously designed and set up such that the decision E for the action A'(E), which defines a reflexive motion and/or protective motion of the prosthesis that is autonomously controlled, is then triggered when:

- a current motion of the prosthetic links deviates from the predicted motion $B_{eweg}(M_A(t))$ or $B_{eweg}(M_A(t))$ of the prosthetic links by more than a specified limit (this limit may be time-variant and/or depend on the state ZUS(t)); and/or
- a current motion of the prosthetic links deviates from a learned model, which observes the nominal states of the prosthesis and corresponding critical deviations from the nominal states; and/or
- it is discernible based on the current state ZUS(t) and the data $D_{UMG}(t)$ that the action A or action A'(E) to be executed by the prosthesis was not or will not be executed, or was or will be executed, in a flawed manner (thereby, for example, a re-grasping can occur when there is a faulty grasping of an object by the prosthesis); and/or
- an unintentional collision of one or more prosthetic links with an object in the environment has occurred or will occur; and/or
- a temperature recorded by a temperature sensor of the prosthesis reaches or exceeds a limit; and/or
- a distal end of the prosthesis has approached an object up to a specified distance or environment envelope (this is used particularly for executing so-called standard skills such as, for example, the (partially) autonomous grasping of an object, the moving of a key on a keyboard, the opening of a door, the grasping and bringing to the mouth of a bottle of beer, etc.); and/or
- the current state ZUS(t) of the prosthesis corresponds to a state to which the following applies: $ZUS(t) \notin Z_{AUS,erlaubt}$, wherein $Z_{AUS,erlaubt}$ indicates the quantity of all allowed states ZUS(t)–ZUS(t) may also be derived variables. Thus, any varieties, observing elements, models can be learned with methods of autonomous learning.

The prosthesis finally includes a control unit, which derives control signals Sig(t) for controlling the actuators, and controls/regulates the actuators based on the control signals Sig(t), which are based on the currently valid, predicted motions $B_{eweg}(M_A(t))$ or $B_{eweg}(M_A(t))$, or based on the reflexive and/or protective motion autonomously controlled in an open-loop/closed-loop manner.

Through evaluation of the $SIG_{BIO}(t)$, through use of the listed sensors to sense the current state ZUS(t) of the prosthesis and the state of an environment of the prosthesis, and through model formation and prediction, the proposed prosthesis enables an improved and more natural control of the prosthesis, wherein the prosthesis is capable of performing autonomous motions and actions, particularly reflexive and/or protective autonomous motion.

An advantageous refinement of the prosthesis is characterized in that the control unit has an input interface, via which a user of the prosthesis prompts, by an input, the control unit to stop any sort of motion of the prosthesis. This enables the wearer of the prosthesis to stop an activity of the prosthesis at any time.

An advantageous refinement of the prosthesis is characterized in that the control unit is designed and set up such that a further motion of the prosthesis takes place based on currently sensed biosignals $SIG_{BIO}(t)$ and/or after an input of a user of the prosthesis by an interface of the control unit after an execution of a reflexive and/or protective autonomous motion, wherein the interface is designed and set up for manual, and/or optical, and/or acoustic, and/or tactile input. Advantageously, the control unit is formed from multiple multimodal control units. It is further advantageous when the control unit is designed and set up such that the control system of the actuators has torque control with friction compensation, and/or impedance regulation, and/or force regulation.

An advantageous refinement of the prosthesis is characterized in that the control unit provides multiple apps (control programs and control parameter sets) for controlling the prosthesis, wherein each app defines an operating mode of the prosthesis, and wherein the control unit has an interface, particularly a wireless interface, to a mobile unit, via which a respective app can be selected and configured for controlling the prosthesis. The mobile unit is advantageously a notebook, or a smart phone, or a mobile tablet computer.

An advantageous refinement of the prosthesis is characterized in that the control unit is designed and set up such that an automatic adapting of the mechanical active and/or passive impedance, particularly the stiffness of the prosthesis, takes place through a corresponding change in the control signals Sig(t), based on the current state ZUS(t) and the data $D_{UMG}(t)$.

The proposed prosthesis is advantageously designed as a hand prosthesis, an underarm prosthesis with and without elbows, a complete arm prosthesis, a leg prosthesis, or a prosthesis with an exoskeleton. One, more, or all of the prosthetic links of the proposed prosthesis can be driven by actuators.

An advantageous refinement of the prosthesis is characterized in that a response interface is available, by which feedback on the current state ZUS(t) of the prosthesis and its interaction with the environment is transmitted to the prosthesis wearer. This feedback occurs preferably haptically or through electrical stimulation.

Other advantages, features, and details result from the following description, in which at least one example embodiment is described in detail—optionally with reference to the drawing. Equivalent, similar, and/or functionally equivalent parts have been given the same reference numbers.

BRIEF DESCRIPTION OF THE DRAWINGS

In the drawings:
FIG. 1 shows a schematic diagram of a proposed prosthesis.

DETAILED DESCRIPTION

FIG. 1 shows a schematic diagram of a proposed prosthesis 100 to replace a missing extremity of a living being, particularly of a human being, which includes one or more prosthetic links driven by actuators 101, wherein a proximal prosthetic link has a mechanical interface for fixing the proximal prosthetic link to the living being; first sensors 102, which sense a current state ZUS(t) of the prosthesis, particularly a state of contact between the prosthesis and an environment; second sensors 103, which sense biosignals $SIG_{BIO}(t)$ of the living being to control the missing extremity; third sensors 104 for sensing data $D_{UMG}(t)$, which describe a current environment of the prosthesis, particularly objects and/or other living beings in the environment; a prediction unit 105, which determines, based on the biosignals $SIG_{BIO}(t)$, the state ZUS(t) of the prosthesis, and the data $D_{UMG}(t)$, a model $M_A(t)$ of an action A to be executed with the prosthesis and predicts motions $B_{eweg}(M_A(t))$, dependent on a model $M_A(t)$, of the prosthetic links for a period of time [t, t+Δt]; an evaluating unit 106 by which the discrete decision E to replace the action A with another action A'(E) can be determined based on an evaluation of the biosignals $SIG_{BIO}(t)$, the state ZUS(t), the data $D_{UMG}(t)$, and the predicted motions $B_{eweg}(M_A(t))$ in accordance with a specified evaluation scheme, wherein the action A'(E) can define a reflexive motion and/or protective motion of the prosthesis that is autonomously controlled in an open-loop/closed-loop manner, and wherein, if the action A'(E) does not define such a reflexive motion and/or protective motion of the prosthesis that is autonomously controlled in an open-loop/closed-loop manner, the prediction unit 105 determines a model $M_A(t)$ of the action A'(E) to be performed by the prosthesis and predicts motions $B_{eweg}(M_A(t))$, dependent on the model $M_A(t)$, of the prosthetic links for a time period [t, t+Δt]; and a control unit 107, which derives control signals Sig(t) to control the actuators and further controls/regulates the actuators based on the control signals Sig(t), wherein the control signals Sig(t) are based on the currently valid, predicted motions $B_{eweg}(M_A(t))$ or $B_{eweg}(M_A(t))$, or based on the reflexive and/or protective motion autonomously controlled in an open-loop/closed-loop manner. The prosthesis can include a processing device 108, which can perform the operations of the units 105-107 as described herein. In particular, the processing device 108 can include a processor and a memory storing instructions that, when executed by the processor, perform any one or more of the operations of units 105-107 as described herein.

Although the invention has been illustrated and explained in more detail by preferred example embodiments, the invention is not limited by the disclosed examples and other variations may be derived by one of ordinary skill in the art without extending beyond the protective scope of the invention. It is thus clear that a plurality of variation options exist. It is likewise clear that example embodiments actually only represent examples, which are not to be interpreted in any manner as a limitation, for example, of the protective scope, the use options, or the configuration of the invention. Rather, the previous description and the description of figures should make one of ordinary skill in the art capable of specifically implementing the example embodiments, wherein one of ordinary skill in the art with knowledge of the disclosed concept of the invention can undertake various changes, for example with respect to the function or the arrangement of individual elements listed in an example embodiment, without going beyond the scope of protection, which is defined by the claims and the legal equivalents thereof such as, for example, more extensive explanations in the description.

LIST OF REFERENCE NUMBERS

101 Actuators
102 First sensors
103 Second sensors
104 Third sensors
105 Prediction unit
106 Evaluating unit
107 Control unit
108 Processing device

The invention claimed is:

1. A prosthesis to replace a missing extremity of a living being, the prosthesis comprising:
one or more prosthetic links configured to be driven by actuators, wherein a proximal prosthetic link has a mechanical interface to fix the proximal prosthetic link to the living being;
first sensors configured to sense a current state ZUS(t) of the prosthesis, wherein the current state ZUS(t) is a state of contact between the prosthesis and an environment;
second sensors configured to sense biosignals $SIG_{BIO}(t)$ of the living being associated with controlling the missing extremity;
third sensors configured to sense data $D_{UMG}(t)$ that describe a current environment of the prosthesis, including objects and/or other living beings located in the environment;
a processing device; and
a memory storing instructions that, when executed by the processing device, perform operations comprising:
determining a model $M_A(t)$ of an action A to be performed by the prosthesis based on the biosignals $SIG_{BIO}(t)$, the state ZUS(t) of the prosthesis, and the data $D_{UMG}(t)$, and predicting motions $B_{eweg}(M_A(t))$, dependent on the model $M_A(t)$, of the prosthetic links for a time period [t, t+Δt];
determining a discrete decision E to replace the action A with an action A'(E) based on an evaluation of the biosignals $SIG_{BIO}(t)$, the state ZUS(t), the data $D_{UMG}(t)$, and the predicted motions $B_{eweg}(M_A(t))$ in accordance with a specified evaluation scheme, wherein the action A'(E) is enabled to define a reflexive motion and/or protective motion of the prosthesis that is autonomously controlled in an open-loop/closed-loop manner, and wherein, if the action A'(E) does not define the reflexive motion and/or protective motion of the prosthesis that is autonomously controlled in an open-loop/closed-loop manner, then determining a model $M_A(t)$ of the action A'(E) to be performed by the prosthesis, and predicting motions $B_{eweg}(M_A(t))$, dependent on the model $M_A(t)$, of the prosthetic links for the time period [t, t+Δt]; and
deriving control signals Sig(t) and controlling/regulating the actuators to drive the prosthetic links based on the control signals Sig(t), wherein the control signals Sig(t) are based on currently valid, predicted motions $B_{eweg}(M_A(t))$ or $B_{eweg}(M_A(t))$, or based on the reflexive motion and/or protective motion that is autonomously controlled in an open-loop/closed-loop manner.

2. The prosthesis according to claim 1, wherein the prosthesis includes an input interface configured to receive a user input prompting the processing device to stop motion of the prosthesis.

3. The prosthesis according to claim 1, wherein the operations further comprise determining the decision E for the action A'(E), which defines the reflexive motion and/or protective motion of the prosthesis that is autonomously controlled in an open-loop/closed-loop manner independently of the biosignals $SIG_{BIO}(t)$, based on the current state ZUS(t) and/or the data $D_{UMG}(t)$.

4. The prosthesis according to claim 1, wherein the operations further comprise triggering the decision E for the action A'(E), which defines a reflexive motion and/or protective motion of the prosthesis that is autonomously controlled, when:
a current motion of the prosthetic links deviates from the predicted motion $B_{eweg}(M(t))$ or $B_{eweg}(M_A(t))$ of the prosthetic links by more than a specified limit; and/or a current motion of the prosthetic links deviates from a learned model, which observes nominal states of the prosthesis and corresponding critical deviations from the nominal states; and/or it is discernible based on the current state ZUS(t) and the data $D_{UMG}(t)$ that the action A or the action A'(E) to be executed by the prosthesis was not or will not be executed, or was or will be executed, in a flawed manner, and/or an unintentional collision of one or more prosthetic links with an object in the environment has occurred or will occur; and/or a temperature recorded by a temperature sensor of the prosthesis reaches or exceeds a limit G2; and/or a distal end of the prosthesis has approached an object up to a specified distance or environment envelope; and/or the current state ZUS(t) of the prosthesis corresponds to a state to which the following applies: $ZUS(t) \notin Z_{AUS,erlaubt}$, wherein $Z_{AUS,erlaubt}$ indicates the quantity of all allowed states ZUS(t).

5. The prosthesis according to claim 1, wherein the operations of controlling/regulating the actuators associated with a further motion of the prosthesis based on currently sensed biosignals $SIG_{BIO}(t)$ and/or after an input of a user of the prosthesis via an input interface of the prosthesis after an execution of a reflexive and/or protective autonomous motion, wherein the input interface is designed and set up for manual, and/or optical, and/or acoustic, and/or tactile user input.

6. The prosthesis according to claim 1, wherein the first sensors comprise one or more of the following sensors:
one or more joint sensors configured to sense motor position, motor speed, and/or motor acceleration;
output sensors;
acceleration sensors;
force sensors configured to determine forces transferred to the environment due to individual prosthetic links and configured to determine forces transferred from the environment onto the individual prosthetic links as well as to determine interaction forces between the prosthesis and the living being wearing the prosthesis;
torque sensors configured to determine torques transferred to the environment due to the individual prosthetic links and to determine torques transferred from the environment onto the individual prosthetic links;
tactile sensors configured to locally sense effective forces and torques;
temperature sensors configured to sense temperatures acting upon the prosthesis; and
humidity sensors configured to sense humidity acting upon the prosthesis.

7. The prosthesis according to claim 6, wherein tactile sensors are comprised in an artificial skin to locally sense effective forces and torques.

8. The prosthesis according to claim 1, wherein the operations of controlling/regulating the actuators comprise:
providing multiple apps that control the prosthesis, wherein each app defines an operating mode of the prosthesis;
selecting a respective app based on input to an input interface of the prosthesis from a mobile unit; and
configuring the app as selected to control the prosthesis.

9. The prosthesis according to claim 8, wherein the app comprises a control program and a control parameter set.

10. The prosthesis according to claim 1, wherein the second sensors comprise one or more electromyography sensors and/or one or more electroencephalography sensors, wherein individual electromyography sensors and/or electroencephalography sensors are applied to the living being or implanted in the living being.

11. The prosthesis according to claim 1, wherein the operations comprise automatically adapting the mechanical active and/or passive impedance through a corresponding change in the control signals Sig(t), based on the current state ZUS(t) and the data $D_{UMG}(t)$.

12. The prosthesis according to claim 11, wherein the mechanical active and/or passive impedance is stiffness of the prosthesis.

13. The prosthesis according to claim 1, wherein the operations further comprise determining the model $M_A(t)$/$M_{A'}(t)$ as a learning-capable process, which autonomously learns motions $B_{eweg}(M_A(t))$/$B_{eweg}(M_{A'}(t))$ of the prosthetic links based on historical data, for executing the action A/A'(E).

14. The prosthesis according to claim 1, wherein the living being is a human being.

* * * * *